United States Patent [19]
Roberts et al.

[11] Patent Number: 5,902,333
[45] Date of Patent: May 11, 1999

[54] PROSTHESIS DELIVERY SYSTEM WITH DILATING TIP

[75] Inventors: George T. Roberts, Weston, Mass.; Erik Andersen, Jyllinge, Denmark

[73] Assignee: Boston Scientific Corporation, Watertown, Mass.

[21] Appl. No.: 08/517,456

[22] Filed: Aug. 21, 1995

Related U.S. Application Data

[63] Continuation of application No. 08/048,287, Apr. 14, 1993, abandoned, which is a continuation-in-part of application No. 08/046,237, Apr. 13, 1993, abandoned.

[51] Int. Cl.$^6$ ........................................................ A61F 2/06
[52] U.S. Cl. ............................... 623/1; 623/12; 606/191; 606/198
[58] Field of Search ...................... 604/104, 105, 604/106; 606/151, 191, 192, 194, 197, 198, 199, 200; 623/1, 11, 12

[56] References Cited

U.S. PATENT DOCUMENTS

| | | | |
|---|---|---|---|
| 1,878,671 | 9/1932 | Cantor | 606/191 |
| 2,701,559 | 2/1955 | Cooper . | |
| 3,334,629 | 8/1967 | Cohn . | |
| 3,540,431 | 11/1970 | Mobin-Uddin . | |
| 3,638,649 | 2/1972 | Ersek . | |
| 3,657,744 | 4/1972 | Ersek | 128/334 |

(List continued on next page.)

FOREIGN PATENT DOCUMENTS

| | | |
|---|---|---|
| 0 183 372 A1 | 6/1986 | European Pat. Off. . |
| 0 364 787 A1 | 4/1990 | European Pat. Off. . |
| 0 418 677 | 3/1991 | European Pat. Off. . |
| 0 461 791 A1 | 12/1991 | European Pat. Off. ........... A61F 2/06 |
| 0 508 473 A2 | 11/1992 | European Pat. Off. . |
| 32 01 056 | 8/1983 | Germany . |
| WO 83/00997 | 3/1983 | WIPO . |
| WO 83/03752 | 11/1983 | WIPO . |
| 8704935 | 8/1987 | WIPO ................... 606/198 |
| WO 93/17636 | 9/1993 | WIPO . |
| WO 94/12136 | 6/1994 | WIPO . |
| WO 94/24961 | 11/1994 | WIPO . |

OTHER PUBLICATIONS

Schneider, Pfizer, Wallstent® Literature, 1994.
Schneider, Pfizer, Wallstent® Literature, 1993.
Kynrim et al., "A Controlled Trial of an Expansile Metal Stent for Pilliation of Esophageal Obstruction Due to Inoperable Cancer" *The New England Journal of Medicine*, vol. 329, No. 18, pp. 1302–1306, Oct. 1993.
Schneider, Pfizer, Wallstent® Literature, 1992.
Schaer et al., "Treatment of malignant esophageal obstruction with silicone–coated metallic self–expanding stents", *Gastrointestinal Endoscopy*, vol. 38, No. 1, pp. 7–11, 1992.
Loizou et al., "Treatment of malignant strictures of the cervical esophagus by endoscopic intubation using modified endoprostheses", *Gastrointestinal Endoscopy*, vol. 38, No. 2, pp. 158–164, 1992.
Schneider, Pfizer, Wallstent® Literature, 1991.
Adam et al., "Self–Expandable Stainless Steel Endoprostheses for Treatment of Malignant Bile Duct Obstruction" *American Journal of Roentgenology*, vol. 156, Feb. 1991.
Medi–Tech®, Boston Scientific Corporation, Strecker™ Stent Literature, 1991.
Medi–Tech®, Boston Scientific Corporation, Strecker™ Stent Literature, 1990.

(List continued on next page.)

*Primary Examiner*—Paul B. Prebilic
*Attorney, Agent, or Firm*—Fish & Richardson P.C.

[57] ABSTRACT

This invention provides prosthesis delivery systems with tips constructed to permit both easier advance into the body and easier removal from the body after expanding the prosthesis. The tip includes a distal taper that can gently widen a lumen during advance in instances where the lumen is narrower than the tip and a proximal taper that can gently widen the lumen on retraction in instances where the prosthesis does not immediately expand the lumen to provide clearance for the larger diameter tip.

5 Claims, 7 Drawing Sheets

U.S. PATENT DOCUMENTS

| | | |
|---|---|---|
| 3,736,939 | 6/1973 | Taylor . |
| 3,774,596 | 11/1973 | Cook . |
| 3,811,423 | 5/1974 | Dickinson, III et al. ............... 128/343 |
| 3,868,956 | 3/1975 | Alfidi et al. . |
| 3,889,685 | 6/1975 | Miller, Jr. et al. ...................... 128/348 |
| 3,938,529 | 2/1976 | Gibbons ................................... 128/349 |
| 4,140,126 | 2/1979 | Choudhury .............................. 128/325 |
| 4,315,509 | 2/1982 | Smit . |
| 4,501,264 | 2/1985 | Rockey . |
| 4,503,569 | 3/1985 | Dotter ..................................... 128/303 |
| 4,512,338 | 4/1985 | Balko et al. . |
| 4,531,933 | 7/1985 | Norton et al. . |
| 4,553,545 | 11/1985 | Maass et al. . |
| 4,578,061 | 3/1986 | Lemeison ................................ 604/164 |
| 4,580,568 | 4/1986 | Gianturco . |
| 4,603,152 | 7/1986 | Laurin et al. . |
| 4,610,657 | 9/1986 | Densow ..................................... 604/8 |
| 4,649,922 | 3/1987 | Wiktor ................................... 128/344 |
| 4,655,771 | 4/1987 | Wallsten . |
| 4,665,918 | 5/1987 | Garza et al. ............................ 128/343 |
| 4,681,110 | 7/1987 | Wiktor . |
| 4,732,152 | 3/1988 | Wallsten et al. ......................... 128/343 |
| 4,739,762 | 4/1988 | Palmaz . |
| 4,762,128 | 8/1988 | Rosenbluth . |
| 4,768,507 | 9/1988 | Fischell et al. . |
| 4,776,337 | 10/1988 | Palmaz . |
| 4,787,899 | 11/1988 | Lazarus . |
| 4,793,348 | 12/1988 | Palmaz .................................... 128/325 |
| 4,878,906 | 11/1989 | Lindemann et al. . |
| 4,886,062 | 12/1989 | Wiktor . |
| 4,893,623 | 1/1990 | Rosenbluth . |
| 4,922,905 | 5/1990 | Strecker . |
| 4,950,227 | 8/1990 | Savin et al. . |
| 5,026,377 | 6/1991 | Burton et al. . |
| 5,049,138 | 9/1991 | Chevalier et al. . |
| 5,078,720 | 1/1992 | Burton et al. . |
| 5,078,725 | 1/1992 | Enderle et al. . |
| 5,158,548 | 10/1992 | Lau et al. . |
| 5,180,366 | 1/1993 | Woods .................................... 606/194 |
| 5,180,368 | 1/1993 | Garrison .................................. 604/104 |
| 5,192,289 | 3/1993 | Jessen ..................................... 606/155 |
| 5,195,984 | 3/1993 | Schatz ......................................... 623/1 |
| 5,234,457 | 8/1993 | Andersen . |
| 5,344,425 | 9/1994 | Sawyer . |
| 5,360,401 | 11/1994 | Turnland . |
| 5,373,854 | 12/1994 | Kolozsi . |
| 5,387,235 | 2/1995 | Chuter . |
| 5,405,380 | 4/1995 | Gianotti et al. . |
| 5,527,298 | 6/1996 | Vance et al. ............................ 606/191 |
| 5,603,698 | 2/1997 | Roberts et al. ......................... 606/198 |

OTHER PUBLICATIONS

Microvasive®, Boston Scientific Corporation, Strecker™ Stent Literature, 1990.

Matsumoto et al., "Tantalum Vascular Stents: In Vivo Evaluation with MR Imaging", *Radiology*, vol. 170, No. 3, pp. 753–755, 1989.

Zollikofer et al., "Endovascular Stenting Veins and Grafts: Preliminary Clinical Experience", *Interventional Radiology*, pp. 707–712, Jun. 1988.

Roubin et al., "Early and late results of intracoronary arterial stenting after coronary angioplasty in dogs", *Laboratory Investigation–Coronary Artery Disease*, vol. 76, No. 4, pp. 891–897, Oct. 1987.

Rosseau et al., "Self–expanding Endovascular Prosthesis: An Experimental Study", *Radiology*, vol. 164, No. 3, pp. 709–714, Sep. 1987.

Lawrence Jr. et al., "Percutaneous Endovascular Graft: Experimental Evaluation", *Cardiovascular Radiology*, vol. 163, No. 2, pp. 357–360, May 1987.

Sigwart et al., "Intravascular Stents to Prevent Occlusion and Restenosis After Transluminal Angioplasty", *The New England Journal of Medicine*, vol. 316, No. 12, pp. 701–706, Mar. 19, 1987.

Rosch et al., "Experimental Intrahepatic Protacaval Anastomosis: Use of Expandable Gianturco Stents", *Radiology*, vol. 162, No. 2, pp. 481–485, Feb. 1987.

Duprat et al., "Flexible Balloon–expanded Stent for Small Vessels", *Radiology*, vol. 170, No. 3, pp. 753–755, Jan. 1987.

Palmaz et al., "Atherosclerotic Rabbit Aortas: Expandable Intraluminal Grafting", *Radiology*, vol. 160, No. 3 pp. 723–726, Sep. 1986.

Palmaz et al., "Expandable Intraluminal Graft: A Preliminary Study", *Radiology*, vol. 156, No. 1, pp. 73–77, Jul. 1985.

Mills et al., "Avoidance of Esophageal Stricture Following Severe Caustic Burns by the Use of an Intraluminal Stent", *The Annals of Thoracic Surgery*, vol. 28, No. 1, pp. 60–65, Jul. 1979.

Becker et al., "Placement of Double–Pigtail Ureteral Stent Via Cystoscope," *Urology*, XX:310–311, Sep. 1982.

Hackethorn et al., "Antegrade Internal Ureteral Stenting: A Techical Refinement," *Radiology*, 156:827–828 Jul. 1985.

Leadbetter, "Diagnostic Urologic Instrumentation," pp. 358–374 (date unknown).

Microvasive, "Ultraflex Esophageal Prosthesis," Brochure (date unknown).

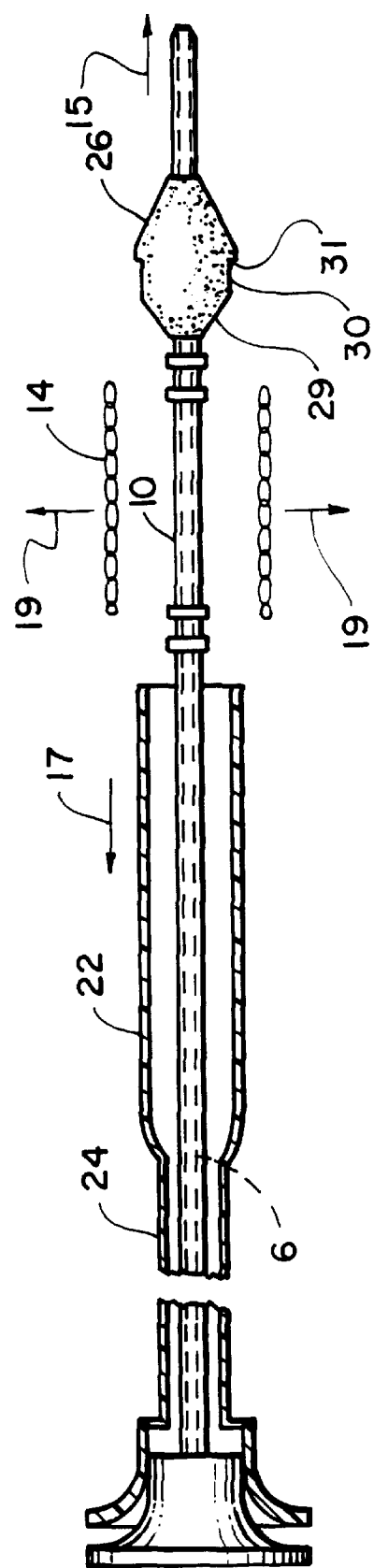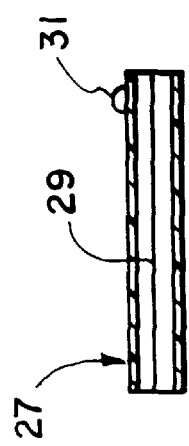

PROSTHESIS DELIVERY SYSTEM WITH DILATING TIP

CROSS-REFERENCE TO RELATED APPLICATIONS

This application is a continuation of Ser. No. 08/048,287 filed Apr. 14, 1993 which is now abandoned which is a continuation-in-part of Ser. No. 08/046,237 filed Apr. 13, 1993 which is now abandoned, the entire contents of which is hereby incorporated by reference.

FIELD OF THE INVENTION

This invention relates to systems for delivering prostheses into the body.

BACKGROUND OF THE INVENTION

Prostheses, such as stents, grafts, and the like, are placed within the body to improve the function of a body lumen. For example, stents with substantial elasticity can be used to exert a radial force on a constricted portion of a lumen wall to open the lumen to near normal size.

These stents can be delivered into the lumen using a system which includes a catheter, with the stent supported near its distal end, and a sheath, positioned coaxially about the catheter and over the stent, to prevent abrasion between the stent and body wall as the catheter is directed through torturous body pathways. The catheter may have an enlarged tip adjacent the distal end of the stent that also helps to atraumatically advance the system and protects the stent.

Once the stent is located at the constricted portion of the lumen, the sheath is removed to expose the stent, which is expanded so it contacts the lumen wall. The catheter is subsequently removed from the body by pulling it in the proximal direction, through the larger lumen diameter created by the expanded prosthesis, which is left in the body.

SUMMARY OF THE INVENTION

This invention provides prosthesis delivery systems with tips constructed to permit both easier advance into the body and easier removal from the body after expanding the prosthesis. The tip includes a distal taper that can gently widen a lumen during advance in instances where the lumen is narrower than the tip and a proximal taper that can gently widen the lumen on retraction in instances where the prosthesis does not immediately expand the lumen to provide clearance for the larger diameter tip. The features of the following aspects can be combined in various ways.

In a one aspect the invention features a system for delivering a prosthesis into the body of a patient. The system includes an elongated catheter having a proximal end that remains outside the body, a distal end, and a supporting portion supporting a prosthesis in a radially compacted form for delivery of the prosthesis to a desired location inside the body, and an dilating tip distal of the prosthesis. The tip has a maximum diameter about equal to or greater than the radially compacted prosthesis and is shaped to include a distal portion that smoothly extends distally to smaller diameters,and a proximal portion that smoothly extends proximally to smaller diameters for enhancing withdrawal after expanding the stent.

Various aspects may also include one or more of the following features. The distal and proximal portions of the tip include tapers to smaller diameter. The tip is formed with a proximal taper an angle of 20 degrees or less. The tip is smoothly shaped in the proximal portion without abrupt edges. The prosthesis is expandable to diameters less than the maximum diameter of the tip and the proximal portion of the tip engages the prosthesis during withdrawing the catheter proximally to widen the passage through the prosthesis for removing the catheter. The proximal portion includes taper of about 20° or less. The tip has a maximum diameter of about 8 mm. The proximal and distal portions have an axial length greater than the maximum diameter of the tip. The tip has transition regions between portions of different diameter and the transition regions are smoothly formed, without abrupt edges. The prosthesis is self-expanding. The system has a retractable protective sheath over the prosthesis, that engages the tip to form a seal that protects the prosthesis from exposure to body fluids during delivery into the body. The protective sheath engages the tip at a step region, which has smooth transitions to different diameters. The sheath has a flexible proximal portion with a smaller diameter than a distal portion positioned over the sheath during delivery into the body.

In another aspect, the invention features a method for delivering a prosthesis into the body of a patient that includes, providing an elongated catheter having a proximal end that remains outside the body, a distal end, and a supporting portion supporting a prosthesis in a radially compacted form, the catheter further including a dilating tip distal of the supporting portion and having a diameter about equal to or greater than the radially compacted prosthesis, and being shaped to include a distal portion that smoothly extends distally to smaller diameters, and a proximal portion that smoothly extends proximally to smaller diameters for enhancing withdrawal after expanding the stent. The method also includes placing the catheter into a body lumen and positioning the prosthesis at a desired location, expanding the prosthesis to a diameter no larger than the maximum diameter of the tip, withdrawing the catheter to engage the proximal portion of the tip and the prosthesis, and continuing to withdraw the catheter so the tip widens the passage through the prosthesis so the catheter can be removed from the body.

Various aspects of the invention may also include one or more of the following features. The method includes selecting a self-expanding prosthesis to provide axial force to the interior of the lumen to fully expand the lumen after an extended period of time, and withdrawing the catheter prior to fully expanding the prosthesis. The method includes crossing a region of a lumen constricted to a diameter smaller than the maximum diameter of the tip by urging the distal or proximal portion of the tip against the region to widen the region.

The inventions have many advantages. For example, since the catheter can be easily removed from the body, the physician does not have to wait until the prosthesis expands to a radial dimension larger than the tip or use a separate dilatation catheter to expand the lumen so that the catheter can be removed. With systems according to the invention, the physician can even select a prosthesis that will produce a predetermined slow expansion of the lumen, over a period of hours or even days, which can have therapeutic benefits such as avoiding rupture of a lumen wall that has been weakened by a tumor. The catheter can be removed from the body immediately after release of the slow-expanding prosthesis. The system, since it can be used to widen the lumen while advancing it into the lumen, also may reduce the need for predilating the lumen with other devices.

Further features and advantages follow.

BRIEF DESCRIPTION OF THE DRAWINGS

We first briefly describe the drawings.

FIG. 1 is a cross-sectional side view of a system according to the invention configured for delivery into the body, while FIG. 1a is a similar view of the system in an alternate configuration, and FIG. 1b is a cross-sectional view of a safety sleeve.

DESCRIPTION OF THE PREFERRED EMBODIMENTS

STRUCTURE

Figure 1:
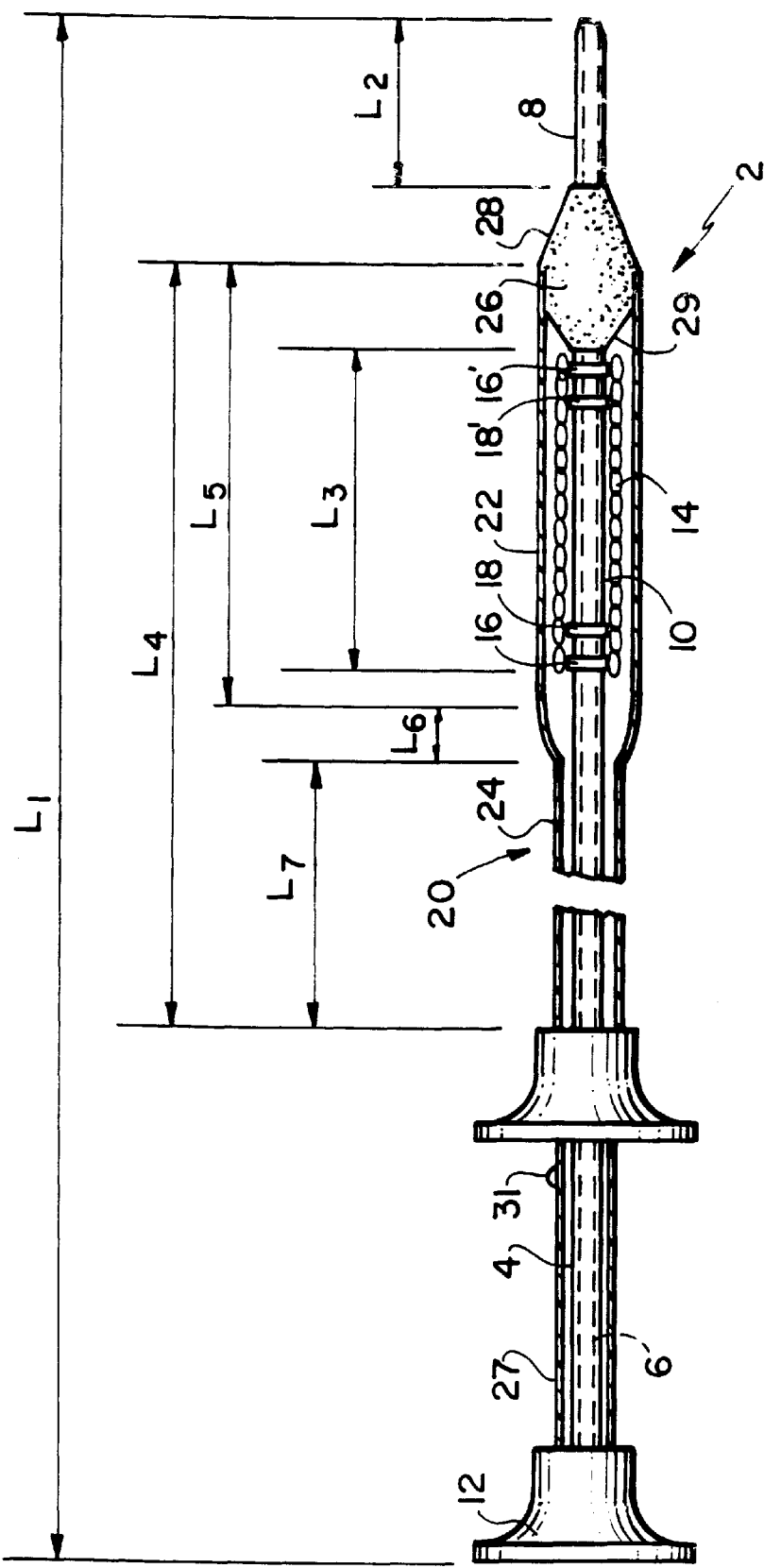

Referring to FIGS. 1 and 1a, a delivery system 2 according to the invention for operation in the esophagus includes a catheter 4 with a stent 14 positioned near the distal end. The system also includes sheath 20, with a reduced diameter portion 24 proximal of a portion 22 for covering the stent 14 during entry into the body (FIG. 1). The sheath 20 can be retracted (arrow 17) to expose and expand (arrows 19) the stent (FIG. 1a). A dilating tip 26, permanently attached to the catheter, has a distal taper 28 to smaller diameter for atraumatic entry of the device into the body, and a proximal taper 29 which can engage the prosthesis and lumen to atraumatically widen the lumen during withdrawal.

The catheter 4 has an overall length, $L_1$, about 100 cm, with a constant outer diameter of about 3.4 mm. The catheter 4 (Pebax, 70 durometer, Atochem, Philadelphia, Pa.) includes a handle 12 (nylon) on the proximal end, an inner lumen 6 (phantom), of about 1.1 mm inner diameter, for tracking over a guidewire (e.g., 0.038 inch). The catheter 4 may include a stainless steel hypotube (not shown) along the wall of its internal lumen and a permanently attached flexible distal end 8, of length, $L_2$, about 3 cm, formed of a soft polymer (Pebax, 40 durometer, Atochem) that flexes easily when challenged by a lumen wall, for atraumatic advance.

The catheter 4 includes a supporting portion 10, of length $L_3$, about 15 cm, for supporting the stent 14 in a radially compacted form during delivery into the body. The stent 14 is preferably a self-expanding knitted stent formed of a highly elastic material such as a nitinol-type material (Strecker Stent, Boston Scientific, Watertown, Mass.). Knitted stents are discussed in detail in Strecker, U.S. Pat. No. 4,922,905 PCT Publication No. 94/12136, the entire contents of these cases being hereby incorporated by reference. The stent has a maximum expanded diameter of about 20 mm. As mentioned, a stent may be selected to apply a constant, rather gentle radial force to the lumen wall that expands the wall to near normal diameter over an extended period, for example, 24 or 48 hours. The stent is radially compacted by wrapping it about the portion 10 and fixing it in this form using a body-fluid degradable gelatin material (DFG STOESS, Deutsch Gelatin Fabriken AG, Germany). The stent in the compacted form has an outer diameter of about 6.5 mm. Compacting the stent by wrapping it onto a catheter and holding it with gelatin is discussed in U.S. Pat. No. 5,234,457 the entire contents of which is also hereby incorporated by reference. Dissolvable polymers are also discussed in U.S. Pat. No. 5,049,138, which is also incorporated herein by reference.

The supporting portion 10 includes radiopaque markers 16, 16' which mark the location of the proximal and distal ends of the stent in the compacted form. The portion 10 also includes radiopaque markers 18, 18' which indicate the ends of the stent 14 in the expanded state.

Positioned coaxially about the catheter 4, and extending over the stent 14 during delivery into the body (FIG. 1), is protective sheath 20. The sheath 20 has an overall length $L_4$, about 70 cm, is formed of a single piece of extruded flexible polymer (extruded Pebax, 70 durometer, available from Atochem) and has a constant wall thickness of about 0.5 mm. The sheath includes a distal portion 22 having a length, $L_5$, about 17 cm, which corresponds approximately to the length of the stent in compacted form with some extension on either end. The outer diameter of the distal portion 22 of the sheath is about 8 mm and the inner diameter is slightly larger than the diameter of the stent 14 in its compacted form, to provide a clearance of about 0.5 mm between the inner wall of the sheath and the compacted stent. The sheath 20 further includes a tapered portion of length, $L_6$, about 7–9 cm, from the larger diameter of the distal portion 22 to the smaller diameter, about 5 mm, of a proximal portion 24 which has a length, $L_7$, about 53 cm. A handle 25 (nylon) allows the sheath to be retracted from the proximal end (arrow 17) to expose the stent so that it can be expanded (arrows 19). (The distance between the handle 25 on the sheath, and handle 12, on the catheter, corresponds approximately to the length of the compacted stent.) A safety sleeve 27 (FIG. 1b) with a slit 29 and pull tab 32 is positioned between the handles during delivery to prevent inadvertent exposure of the stent (FIG. 1). The sleeve 27 is stripped from the catheter once the system is properly placed so the sheath can be retracted to expose the stent (FIG. 1a). The diameter of the proximal portion 24 is selected to conform closely to the outer diameter of the catheter body 4. The clearance between the outer diameter of the catheter body 4 and the inner diameter of the proximal portion 24 of the sheath 20 is about 1.5 mm.

The sheath, having variable radial dimension along its length, is a particular feature of the invention which enhances positioning of a large stent with large delivery systems for use in a lumens having torturous pathways. Since the outer diameter of the proximal portion of the sheath is small, the flexibility is enhanced. It flexes more easily around torturous channels because there is less strain on the outside curved wall and less compaction on the inside curved wall. Since all portions of the sheath conform more closely to the outer diameter of the components within the sheath, kinking along the length is reduced. The gap between the outer diameter of the catheter and inner diameter of the sheath is small, so the catheter tends to support the relatively thin-walled sheath when the system is bent around a curve. In the distal portion of the sheath, the larger radial dimension is supported by the larger radial dimension of the stent, which is positioned around the catheter. Minimizing kinking is an important feature, since severe kinking can cause friction between the sheath and the catheter that can prevent the sheath from being retracted. In many body lumens, such as the esophagus, the most torturous portion of the lumen is near the point of entry of the body. The present system improves operation by enhancing flexibility and reducing kinking particularly in the proximal portions of the device typically located along a torturous bend. The sheath of the system described does not kink in the proximal portions when bent 90 degrees over a radius of about 6.35 cm, which is typical of the esophagus. Moreover, a sheath with reduced size in proximal portions presents a smaller inner surface area, which reduces friction against the catheter, and therefore makes operation smoother.

Figure 2:
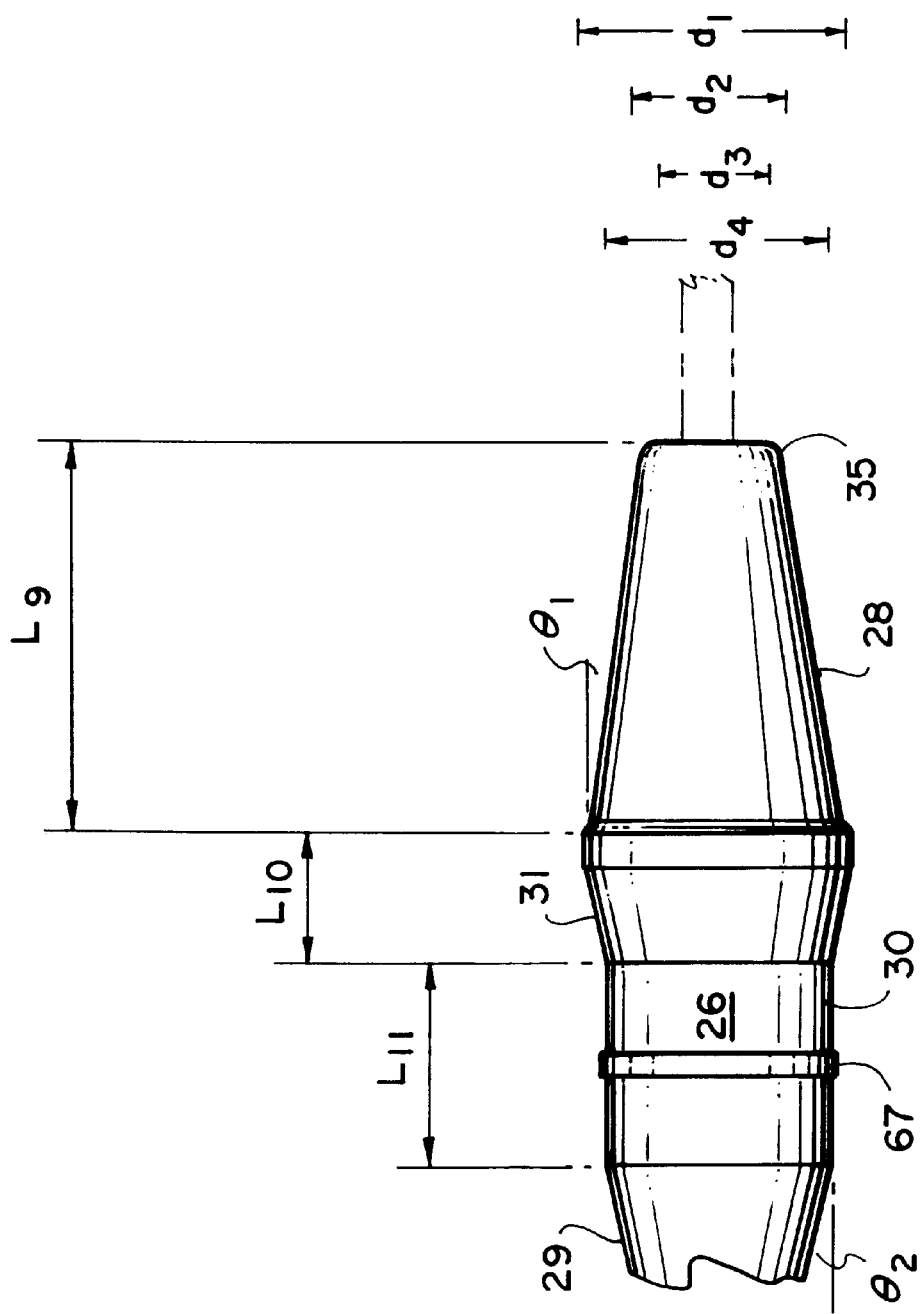
FIG. 2 is a detailed side view of a dilating tip.

Referring particularly to FIG. 2, the system further includes a dilating tip 26 which is generally designed to contact the body lumen atraumatically and also can perform the additional function of dilating the lumen so the catheter can be urged through a narrow stricture, smaller than the tip, to widen and cross a lesion. After expanding the stent, the tip allows dilating the lumen and/or the passage through the stent during withdrawal of the catheter. The tip 26 has a length, $L_8$, about 28 mm, and a maximum outer diameter, $d_1$, about 8 mm. The maximum outer diameter of the tip 26 substantially corresponds to the maximum outer diameter of the distal portion 22 of the sheath 20 (phantom). The tip 26 includes a distal taper portion 28 of length, $L_9$, about 12.5 mm, at an angle $\theta_1$, about 10 degrees, to present a gradual increase in diameter when the system is moved axially distally. The distal taper tapers to a diameter, $d_2$, about 4.5 mm at its end 35, which has atraumatic rounded edges as shown. The tip 26 also provides a gradual profile to smaller diameters in the proximal direction. The tip includes a proximal taper 29 at an angle, $\theta_2$, about 20° (smaller angles can be used) that aids smooth engagement of the tip with portions of the stent and/or lumen and gentle expansion when removing the catheter during withdrawal. The proximal taper 29 has a length, $L_{12}$, about 4 mm, and tapers to a diameter, $d_3$, about 4.0 mm at the end 37 of the taper. The tip, generally, is elongated compared to its maximum diameter and, in particular, the proximal region is elongated compared to the maximum diameter for providing a gradual transition. The most proximal portion 39 of the tip is rounded to the outer diameter of the catheter 4 (phantom). The distal portion of the sheath meets the tip 26 along a shelf portion 30 of length, $L_{11}$, about 7 mm and diameter, $d_4$, about 6.8 mm. The shelf portion 30 also includes a slight taper 31, at an angle of less than 20 degrees, for example, around 10 degrees, with length $L_{10}$, about 4 mm, to the maximum diameter $d_1$. The transitions between all of the portions of the tip of different diameter, especially those in the proximal parts of the tip, are smooth or rounded for gradual, atraumatic movement and to avoid any sharp edges that could hang up when engaging a partially expanded stent or body lumen wall, especially during withdrawal. The smooth profile and rounded surfaces without blunt ends or abrupt edges substantially avoids the tip hanging up on the stent as the catheter is withdrawn. This feature is particularly important with knit-type stents formed of successive rows of loops. The length of the regions proximal and distal of the maximum diameter are relatively long compared to the maximum diameter to provide a gentle, gradual engagement and widening of the lumen during withdrawal. The shelf portion 30 of the tip 26 and the sheath 20 (phantom) form a seal that isolates the stent from body fluids during delivery into the body to avoid dissolving the gelatin prior to withdrawal of the sheath, which could cause premature expansion of the stent.

The tip 26 can be formed of a nondissolvable relatively noncompressible (i.e. rigid) polymer (Nylon, Vestamid, Hulls, Germany) and can be securely attached to the catheter by insert molding the tip onto the catheter. A compressible silicon O-ring 67, about 1 mm diameter, may be fitted into a groove (about 0.85 mm deep) in the shelf portion 30 to enhance the seal with the sheath. The tip may also be polyethylene.

Use

The following procedure may be used for treating a patient with a tumor in the esophagus. The patient is prepared on an endoscopic table. The physician passes an endoscope, which has a diameter of approximately 12 mm, through the patient's mouth into the esophagus to view both the proximal and distal portions of the tumor to determine its morphology and character. If the endoscope will not cross through the tumor, the physician will dilate the lumen with a rigid dilator tracked over a guidewire or a balloon dilator which tracks through the endoscope. The endoscope is then passed retroflex so it looks back on itself and up at the most distal portion of the tumor to view its makeup. The physician measures the length of the tumor using graduated centimeter markings on the endoscope and/or makes a notation of the patient's incisor as to the most distal segment of the tumor. The physician then withdraws the endoscope partially and finds the most proximal segment of the tumor and makes a similar notation to determine the length of the tumor. Generally, the length of the stent is selected so that it extends about 2 cm beyond each end of the tumor. As discussed, the tip 26 may also be used to widen the lumen in some cases, either initially or after the esophageal wall rebounds after dilatation by other means.

Figure 3:
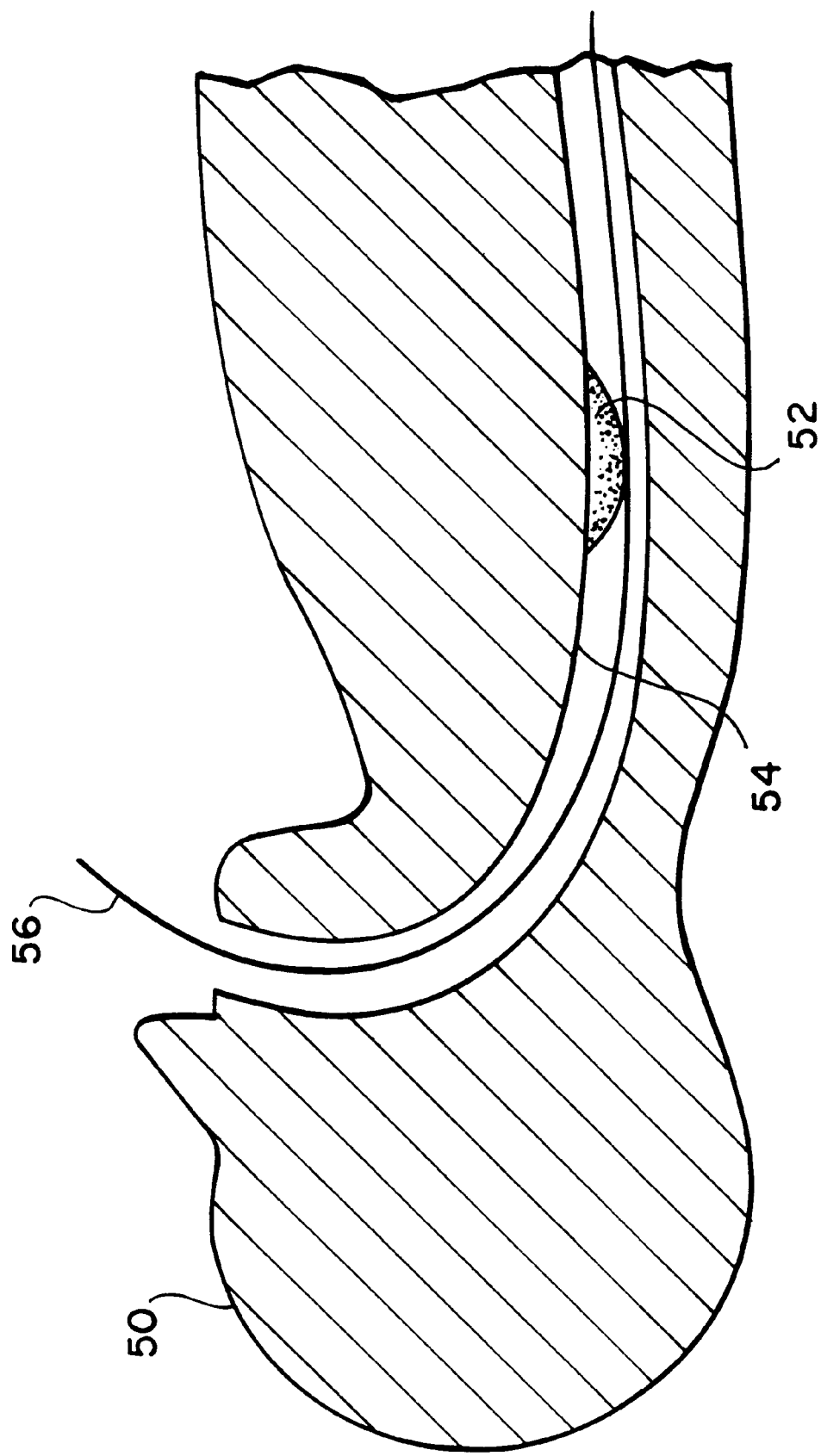
FIGS. 3–3h illustrate positioning a stent in the esophagus of a patient with a system according to the invention.
Figure 3A:
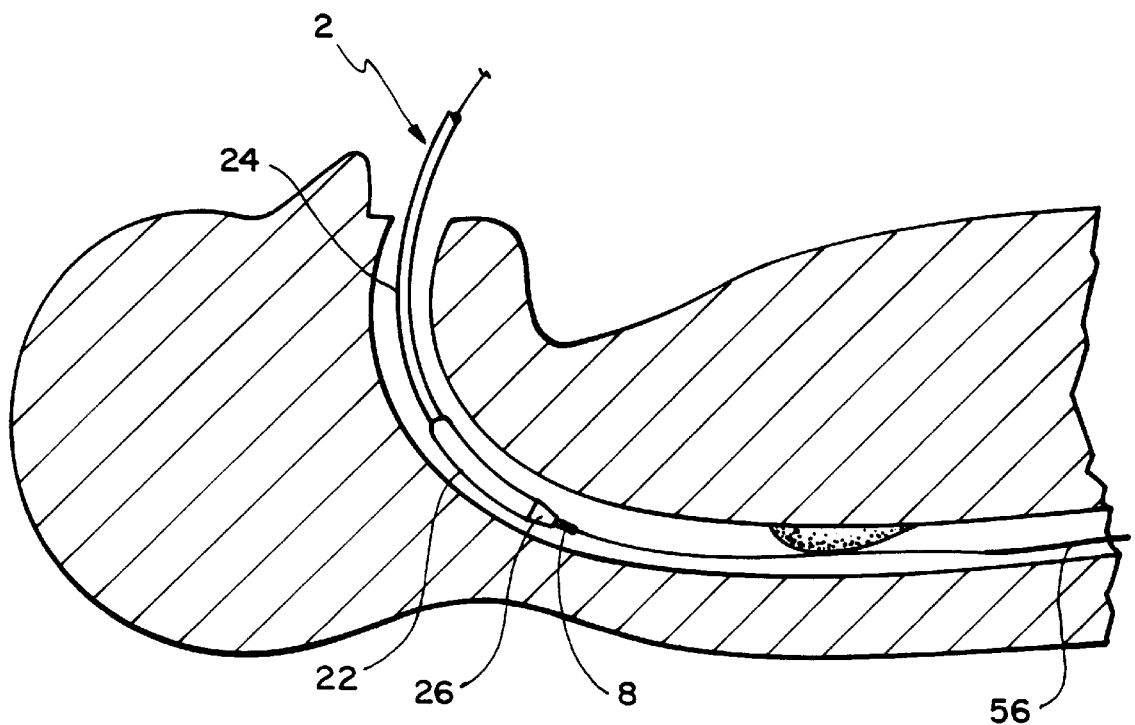
Figure 3B:
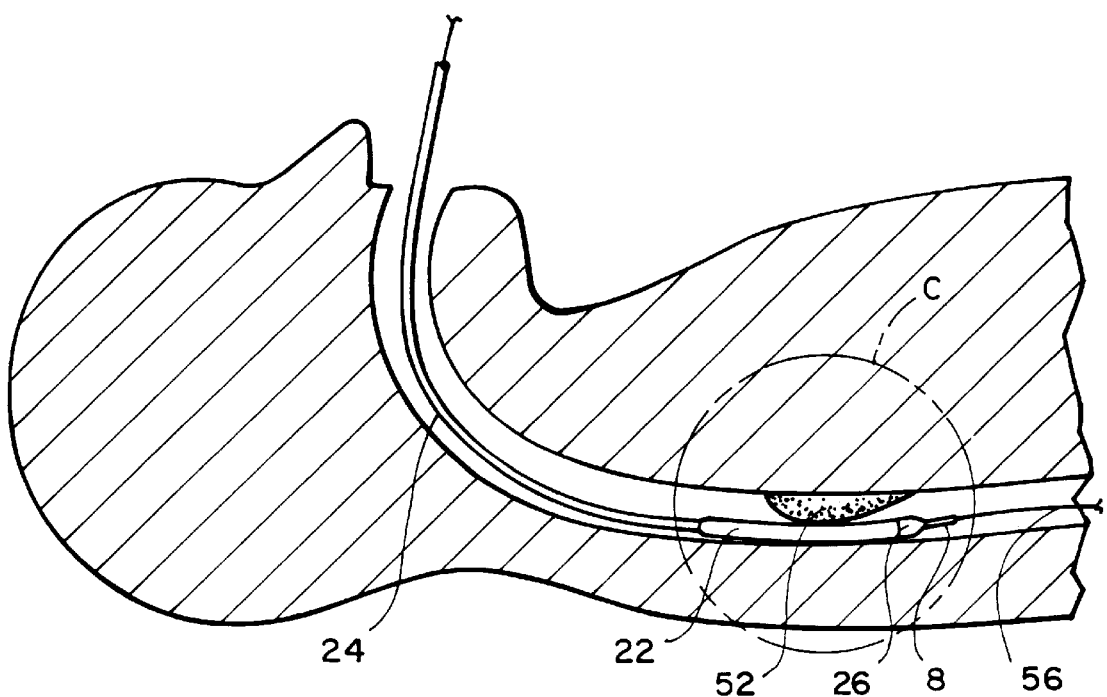
Figure 3C:
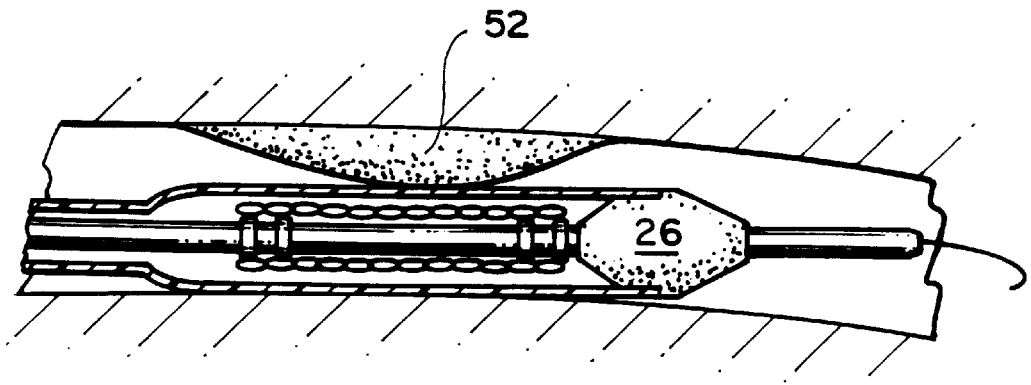
Figure 3D:
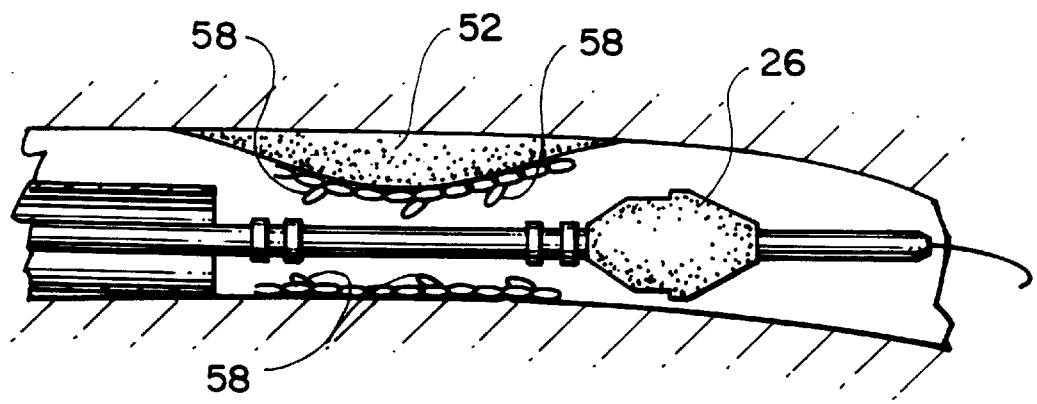
Figure 3E:
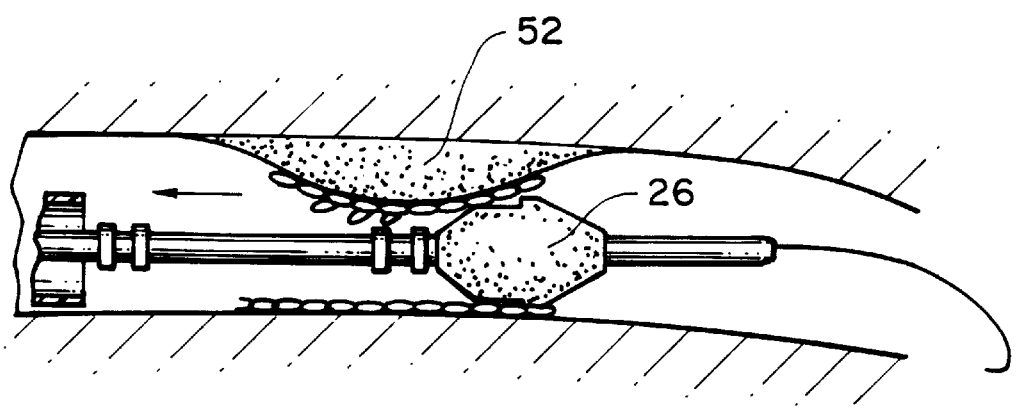
Figure 3F:
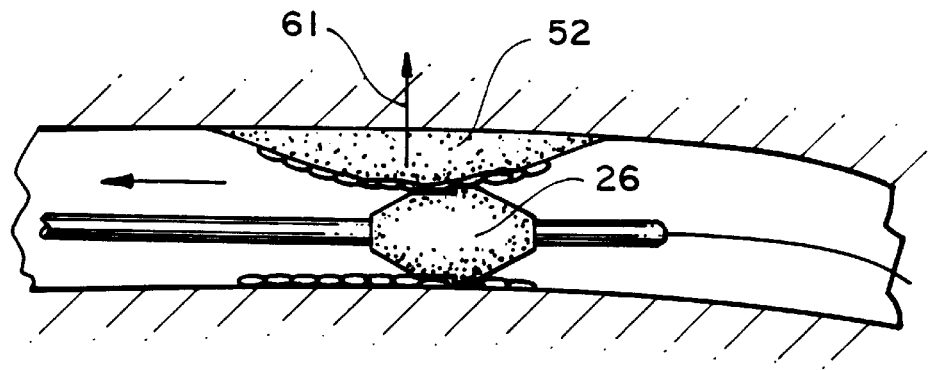
Figure 3G:
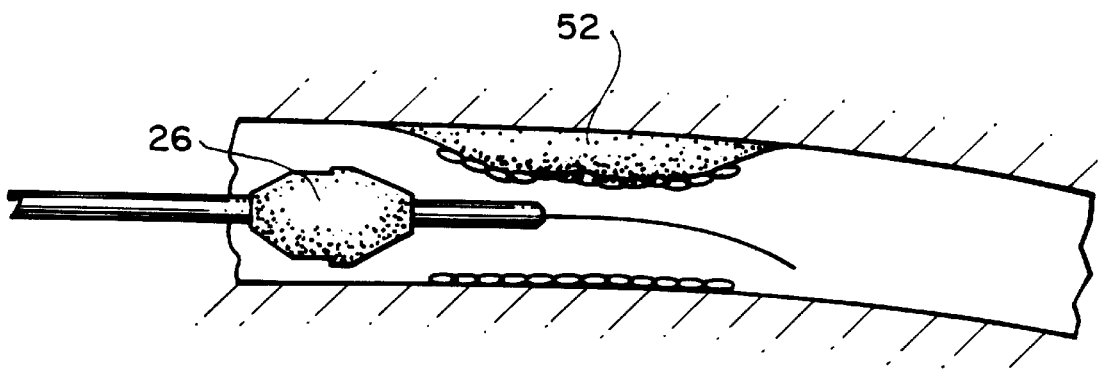
Figure 3H:
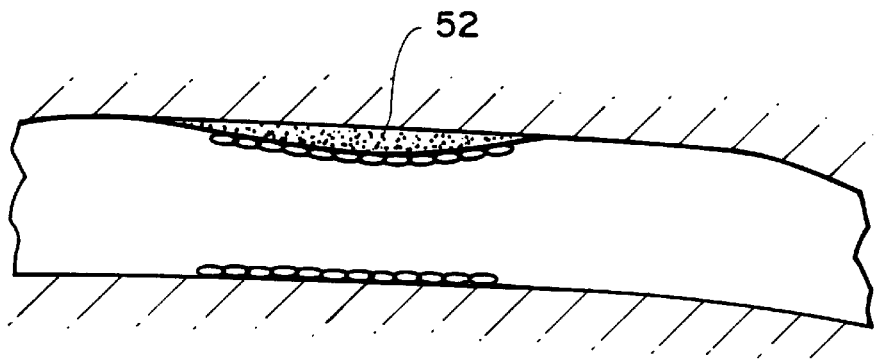

Referring to the series of FIGS. 3–3*h*, placement of a stent in the esophagus of a patient is illustrated. Referring to FIG. 3, the patient 50 having a tumor 52 in the esophagus 54, normally about 20 mm lumen diameter, but constricted to 8–12 mm by the tumor is treated by positioning a guidewire 56 through the throat into the esophagus to a position distal of the tumor 52, usually into the stomach.

Referring to FIG. 3*a*, the delivery system 2 is delivered over the guidewire by sliding the proximal portion of the guidewire through the guidewire lumen in the catheter. A lubricant, K-Y jelly, may be applied to the distal end 8 of the catheter and the tip 26. The physician then observes the placement with a fluoroscopic device using the radiopaque markers. As illustrated, the esophagus includes a highly torturous portion just distal of the throat including a 90 degree bend over a radius of about 6.35 cm. The distal end of the system, including the enlarged portion 22 of the sheath covering the stent, has sufficient strength to follow the contour of the wire without excessive kinking, which is enhanced by the support of the underlying stent. It should be appreciated that in this case, even if some kinking of the distal portion 22 of the sheath should occur as it passes the torturous bend, the kinks do not substantially impede the operation since the stent has not been located at a position at which the sheath would be withdrawn. As illustrated, the tip 26 provides a gradual increase in diameter, providing an atraumatic advance of the system into the esophagus.

Referring to FIGS. 3*b* and 3*c* (an enlarged view of the area in circle c) the distal portion of the system, corresponding to the position of the stent and the enlarged portion 22 of the sheath, is located across the constriction caused by the tumor 52. In this position, the portions of the system including the reduced diameter portions 24 of the sheath are easily bent around the initial curve. The tip 26, with the gradual transition to larger diameter, aids in crossing the constricted region. As discussed, the tip may also be used to urge open the region.

Referring to FIGS. 3*d* to 3*h*, enlarged views of the constricted region are shown to further illustrate the operation. Referring particularly to FIG. 3*d*, with the stent properly located about the constriction, the sheath is slid axially proximally to expose the stent to the body lumen. The gelatin holding the stent in compacted form is dissolved by body fluids and the stent self-expands to larger diameter. As illustrated, in many instances, the stent initially expands the constriction to a small degree with a waist-shaped constriction still providing a rather narrow passageway with radial dimension somewhat smaller than the maximum radial dimension of the tip 26. The initial opening through the constriction may be formed, as mentioned, by a dilating means, so the opening is initially large enough to allow the system to cross with some clearance. However, the opening can be reduced somewhat after the system has crossed by a rebounding of the esophageal wall. In some cases,, the system, with the atraumatic tip may be used to widen the constricted portion slightly so that the system can pass. Further, the stent, upon release from the catheter unwraps partially, leaving fold portions 58 that occlude the lumen partially. All of these conditions can create situations in which the tip is of a larger diameter than the constricted region of the lumen.

Referring to FIG. 3e, under these conditions, upon withdrawing the catheter, the proximal portion of the tip 26 engages the stent in the region of the constriction. The smooth gradual profile to larger diameters and rounded transitions keep the tip from hanging up or catching on the stent as the tip is drawn proximally.

Referring to FIG. 3f, as withdrawal of the catheter continues, the proximal portion of the tip gradually enlarges the passage thought the constricted area by either or a combination of expanding the body lumen (arrow 61) and the stent or gently pushing the folds of the stent out of the way to form a larger passageway, allowing the tip to pass through and the catheter to be withdrawn.

Referring to FIGS. 3g to 3h, after a short time the radial force provided by the stent further widens the esophagus providing a large open lumen that facilitates swallowing.

Other Embodiments

Many other embodiments are possible. For example, the maximum diameter of the tip may be selected to be much larger than the diameter of the stent in the compacted form so the tip dilates the lumen to a desired diameter before expanding the stent. The sheath may be modified to enhance pushability or pullablity when the tip is used to widen lumens. The tip may be formed integrally with the catheter. The delivery systems can be sized and configured for use in various body lumens, the prostate, urethra or the biliary tree including the common bile duct, pancreatic duct and left and right hepatic ducts, and with particular benefit in alimentary tract lumens, such as the esophagus, stomach, pilorus, small intestine, colon or rectum. As will be appreciated, most of the latter applications involve relatively large lumens, about 1 to 1.5 cm or more, with torturous bends requiring relatively large stents to be delivered with large flexible delivery systems that resist kinking. As mentioned above, aspects of this invention provide particular advantages for delivering large stents, greater than about 10 mm expanded diameter, using larger delivery systems, greater than 6 mm maximum diameter. Like the esophagus, most of these lumens also have an extreme curvature near the entry point of the delivery system, such as the rectal sigmoid area in the colon. In the structure discussed in detail above, the stent is self-expanding and held compacted using a gelatin, but other embodiments uses a sheath that holds the stent in compacted form, without use of the gelatin. For example, the sheath may be constructed to hold the stent in compacted form by having a thicker wall in the distal portions and a thinner wall in proximal portions. The sheath may be formed in various ways, such as from polyethylene shrink tubing, which is reduced in diameter in proximal portions by heat application. In such cases, the wall thickness of the tubing is increased in the proximal portions, which can enhance the strength. The advantages of the invention can also be realized with stents that are not self-expanding, such as balloon expandable stents. A fluid, such as saline can be flowed into the lumen to more rapidly dissolve body-fluid dissolving portions.

Still further embodiments are within the following claims.

What is claimed is:

1. A system for delivering a prosthesis into a body lumen of a patient, comprising:

an elongated catheter with a catheter shaft defining an axis and having a proximal end that remains outside the body, a distal end, and a supporting portion for supporting a prosthesis configured in a radially compact form for delivery of the prosthesis to a desired location inside the body, a bi-directional, rigid dilating tip fixed to said catheter at a point distal of said prosthesis, said tip having a distal dilating portion, a proximal dilating portion, and a maximum diameter portion therebetween, said maximum diameter portion having a diameter that is about equal to or greater than the radially compact form of said prosthesis, said distal dilating portion extending distally over an axial length to a smaller diameter and having a smooth profile that is free of sharp edges, said smaller diameter being about equal to the diameter of the catheter shaft, and said axial length being greater than the diameter of said maximum diameter portion of said tip, and said proximal dilating portion extending proximally over an axial length to a smaller diameter and having a smooth profile that is free of sharp edges, said smaller diameter being about equal to the diameter of the catheter shaft, and said axial length being greater than the diameter of said maximum diameter portion of said tip, said proximal dilating portion constructed for gradually dilating said lumen during proximal motion of said catheter while withdrawing the catheter after releasing said prosthesis, said proximal dilating portion of said tip including a shelf-portion of constant diameter over an axial length, said shelf portion having a diameter corresponding to the inner diameter of said sheath such that distal portions of said sheath can engage said shelf portion when extended over said prosthesis to protect said prosthesis against exposure to body fluids, said shelf portion comprising a compressible polymer o-ring fitted into a groove in said shelf portion, and a thin walled retractable protective sheath sized to be coaxially disposed about and closely conform to said prosthesis when supported on said catheter in said radially contracted form during said delivery to said desired site, and said tip further constructed in cooperation with said sheath such that said sheath engages said tip when said sheath is coaxially disposed about said prosthesis and the outer diameter of said sheath is no greater than the diameter of said maximum diameter portion of said tip to protect said sheath during said distal motion while delivering said prosthesis.

2. A method for delivering a prosthesis into the esophagus of a patient, comprising:

providing an elongated catheter with a shaft defining an axis and having a proximal end that remains outside the body, a distal end, and a supporting portion for supporting a prosthesis configured in a radially compact form, said catheter further including a bi-directional dilating tip fixed to said catheter at a point distal of said prosthesis, said tip having a distal dilating portion, a proximal dilating portion, and a maximum diameter portion therebetween, a prosthesis carried upon said catheter, said maximum diameter portion having a diameter that is about equal to or greater than the radially compact form of said prosthesis, said distal dilating portion extending distally over an axial length and with a smooth profile that is free of sharp edges to a smaller diameter, said smaller diameter being about equal to the diameter of the catheter shaft, and said axial length being greater than the diameter of said maximum diameter portion of said tip, and said proximal dilating portion extending proximally over an axial length and with a smooth profile that is free of sharp edges to a smaller diameter, said smaller diameter being about equal to the diameter of the catheter shaft, and said axial length being greater than the diameter of said maximum diameter portion of said tip, placing said catheter into a body lumen and positioning said prosthesis at a desired location, expanding said prosthesis to a diameter no larger than said maximum diameter of said tip, withdrawing said catheter to engage the proximal dilating portion of the tip and the prosthesis, and continuing to withdraw said catheter so said tip widens the passage through the prosthesis so the catheter can be removed from the body immediately after deployment.

3. The method of claim 2 comprising, selecting a self-expanding prosthesis to provide axial force to the interior of said lumen to fully expand said lumen after an extended period of time, and withdrawing said catheter prior to fully expanding said prosthesis.

4. The method of claim 2 or 3 comprising crossing a region of a lumen constricted to a diameter smaller than the maximum diameter of the tip by urging the distal or proximal portion of said tip against said region to widen said region.

5. The method of claim 2 or 3 wherein the lumen being treated has a diameter of about 1 cm or more.

* * * * *